United States Patent [19]

Fan

[11] Patent Number: 5,091,205

[45] Date of Patent: Feb. 25, 1992

[54] HYDROPHILIC LUBRICIOUS COATINGS

[75] Inventor: You-Ling Fan, East Brunswick, N.J.

[73] Assignee: Union Carbide Chemicals & Plastics Technology Corporation, Danbury, Conn.

[21] Appl. No.: 449,777

[22] Filed: Dec. 22, 1989

Related U.S. Application Data

[63] Continuation-in-part of Ser. No. 297,331, Jan. 17, 1989, abandoned.

[51] Int. Cl.⁵ .................. A01N 1/02; A61K 00/00; A61M 5/32
[52] U.S. Cl. .................. 427/2; 427/412.1; 604/265; 604/266
[58] Field of Search .............. 427/412.1, 393.5, 2; 604/265, 266

[56] References Cited

U.S. PATENT DOCUMENTS

| | | | |
|---|---|---|---|
| 3,642,943 | 2/1972 | Noel | 427/393.5 |
| 3,663,288 | 5/1972 | Miller | 604/266 |
| 4,265,927 | 5/1981 | Eriksson et al. | 427/2 |
| 4,373,009 | 2/1983 | Winn | 427/412.1 |
| 4,442,145 | 4/1984 | Probst et al. | 427/393.5 |
| 4,479,795 | 10/1984 | Mustacich et al. | 604/265 |
| 4,526,579 | 7/1985 | Ainpour | 604/265 |
| 4,642,242 | 2/1987 | Solomon et al. | 427/2 |
| 4,729,914 | 3/1988 | Kliment et al. | 428/35.7 |
| 4,773,901 | 9/1988 | Norton | 604/265 |
| 4,906,237 | 3/1990 | Johansson et al. | 604/265 |
| 4,987,181 | 1/1991 | Bichon | 427/2 |

FOREIGN PATENT DOCUMENTS 166998 4/1984 European Pat. Off.

Primary Examiner—Michael Lusignan
Assistant Examiner—Diana L. Dudash
Attorney, Agent, or Firm—Paul W. Leuzzi, II

[57] ABSTRACT

A new method is provided to impart a hydrophilic lubricious coating onto articles such as medical devices. A device, for example a catheter, is first contacted with a polyisocyanate solution, to provide coupling, then contacted with a poly(carboxylic acid) solution to give a coating, and is then finally oven dried. These coatings have lubricity that only becomes manifest upon exposure to water or body fluids, and moreover, are also long lasting and have good abrasion resistance. This combination of properties is not available from other currently used or proposed coatings.

52 Claims, No Drawings

HYDROPHILIC LUBRICIOUS COATINGS

RELATED APPLICATIONS

This application is a continuation-in-part of U.S. application Ser. No. 297,331, filed Jan. 17, 1989, now abandoned, the entire contents of which is hereby incorporated by reference.

BACKGROUND OF THE INVENTION (1) Field of the Invention

This invention relates in general to coated substrates. In one aspect, this invention is directed to medical devices and other substrates having improved lubricious coatings. In a further aspect, this invention provides medical devices, such as catheters, guide wires and the like, which when dry exhibit little or no lubricity but when moistened, possess a lubricity which aids in moving the devices within the body with ease and little discomfort. In another aspect, this invention is directed to a process for the preparation of the coated medical devices which are useful in the diagnosis or treatment of various conditions in the human body.

(2) Description of the Related Art

Catheters which are used surgically for insertion through blood vessels, urethrea, or body conduits, and guide wires used with catheters for biopsy, balloon angioplasty and other medical procedures require a low-friction surface for preventing injury to, or inflammation of, mucous membranes and other body tissues.

One class of conventional catheters is made of low-friction materials such as TEFLON, polyethylene or other materials coated with a layer of TEFLON or silicone. There are two shortcomings of these catheters: First, they are not sufficiently slippery for the intended surgical purposes mentioned above. Second, they are difficult to handle and store because their surfaces are slippery at all times.

Another class of conventional catheters is rendered lubricious by coating with a layer of silicone fluid, glycerin, or olive oil. These materials are unsatisfactory because the low molecular weight additives tend to run off quickly. Thus, they lose the initial lubricity rather rapidly.

Another class of conventional surface treatment involves the deposition of poly(vinyl pyrrolidone) in the presence of a polyisocyanate. This type of coating while lubricious initially lacks abrasion resistance, and is therefore easily removed from the surface of the medical devices. An improved version of this technique was described by R. A. Winn in U.S. Pat. No. 4,373,009, where an active hydrogen containing vinyl pyrrolidone copolymer was used instead to result in a better bonding to the substrate. The "monomers containing active hydrogen" were needed according to Winn "to form a covalent bond between the coupling coating and the hydrophilic copolymer". These copolymers, however, were of unknown quality in terms of purity, toxicity, or not of sufficiently high molecular weight needed for this application. Both the availability and usefulness of these copolymers are highly questionable.

In U.S. Pat. No. 4,119,094, a substrate such as a tube or catheter is disclosed having a hydrophilic coating which exhibits a low coefficient of friction. The substrate is coated with a poly(vinyl pyrrolidone)-polyurethane interpolymer. A polyisocyanate and a polyurethane mixture is applied to a substrate and after drying, a poly(vinyl pyrrolidone) in solution is applied.

U.S. Pat. No. 4,589,873, issued on May 20, 1986 to A. Schwartz et al and discloses a method of applying a hydrophilic coating to a polymeric substrate. The coating consists of poly(vinyl pyrrolidone) which is applied to the substrate in a solvent followed by drying.

W. S. Creasy et al were granted U.S. Pat. No. 4,642,267 on Feb. 10, 1987 which discloses and claims a hydrophilic polymer blend. The blend is comprised of a thermoplastic polyurethane having no reactive isocyanate groups and a hydrophilic poly(N-vinyl lactam) such as poly(vinyl pyrrolidone) The blend can contain additional polymeric components such as homopolymers or copolymers of monomers including vinyl chloride, acrylic acid, vinyl alcohol and the like.

A process for coating a polymer surface with a hydrophilic coating is also disclosed in U.S. Pat. No. 4,666,437. A solution of a compound containing at least two unreacted isocyanate groups per molecule is applied to the polymer surface and the solvent evaporated. Thereafter, a solution of poly(vinyl pyrrolidone) is applied to the treated surface and the coated cured.

According to European patent application 0166998, N. Takamura described lubricious coatings derived from either a cellulosic polymer, a maleic anhydride polymer, a polyacrylamide or a water-soluble nylon which were convalently bonded to a medical instrument substrate. The substrate contained reactive functional groups such as aldehydes, epoxy, isocyanate or amino groups. The reference indicates that the water soluble polymers are non-crosslinked and contain hydrophilic groups such as —OH, —CONH$_2$, —COOH, —NH$_2$, —COO—, —SO$_3$—, and —NR$_3$, R being alkyl or hydrogen. However, a cellulosic polymer is undesirable because it must be protected against microbe attack. Coatings made from a maleic anhydride polymer must go through a tedious post treatment with water before developing lubricity, while water-soluble nylons may have questionable stability.

It has now unexpectedly and surprisingly been found that high molecular weight carboxylic acid-containing polymers or their partially neutralized salts, can be strongly bonded to a substrate, such as a catheter, using a polyisocyanate reagent and at the same time provides a hydrophilic lubricious coating. Thus, the need for either an interpenetrating network containing poly(vinyl pyrrolidone) and polyurethane or a copolymer containing both non-active hydrogen units and active-hydrogen units can be avoided. Furthermore, there is no need for any post hydrolysis treatment in the invention. Unlike a maleic anhydride polymer, the coating develops lubricity instantly upon exposure to an aqueous fluid. Poly(acrylic acids), such as the CARBOPOLS manufactured by B.F. Goodrich, are ideally suited for the intended medical applications, and also have sufficiently high molecular weights necessary for achieving both good hydrophilic lubricity and abrasion resistance.

Accordingly, one or more of the following objects will be achieved by the practice of this invention. It is an object of this invention to provide medical and other devices which when dry do not exhibit a slippery surface, but when contacted with a fluid such as water, become very lubricious. Another object of this invention is to provide medical and other devices which are easily handled without fear of slipping, but when moistened or contacted with body fluids instantly become very lubricious. A further object of this invention is to provide medical devices having a coating of a poly(carboxylic acid) and a polyisocyanate which when dried can be handled with ease, but when moistened, become very slippery. A still further object of this invention is to provide processes for the preparation of the coated medical and other substrates. Another object is to provide medical and other devices and instruments which have a coating of a material which becomes lubricious upon exposure to body fluids. These and other objects will readily become apparent to those skilled in the art in the light of the teachings herein set forth.

SUMMARY OF THE INVENTION

In its broad aspect, this invention is directed to coated substrates having a lubricious coating which becomes slippery only upon exposure to an aqueous fluid. The invention is also directed to a method for coating the devices and substrates as well as to the coated articles themselves.

One or more polyisocyanates is applied to a substrate such as a medical device. The contact time may vary from a few seconds to an hour or more depending upon the material of construction of the medical device and the polyisocyanate employed. The primer coated medical device can be dried in an oven for removal of any solvent and then the carboxylic acid-containing polymeric top coat applied directly to the polyisocyanate coated device. The coated medical device is then dried to complete the coating process. The finished medical device has normal feel and handling characteristics when dry. Upon exposure to body fluids, however, it becomes lubricious instantly.

DETAILED DESCRIPTION OF THE INVENTION

The hydrophilic lubricious coating of this invention is prepared by first contacting a substrate or medical device, such as a catheter, with a polyisocyanate such as a toluene diisocyanate in a liquid medium. The liquid medium can be removed by drying or the catheter can be treated directly with a high molecular weight poly(carboxylic acid) in a liquid medium. After drying in an oven, a nontacky, easy-to-handle, and uniformly coated catheter is obtained. The surface of the resultant catheter becomes lubricious instantly upon exposure to an aqueous solution or body fluids.

In addition to a quick initial lubricity, the hydrophilic lubricious coating of this invention is resistant to abrasion. Consequently, a catheter coated in accordance with the teachings of this invention will retain a lubricious surface for a long duration which is often required during the course of a surgical procedure.

Unlike catheters made of or coated with Teflon or silicones, catheters coated in accordance with the present invention are non-slippery when dry but become instantly slippery when wet. As a result, medical devices coated with the hydrophilic lubricious coatings of this invention are easier to handle and store.

The term "bath" as employed throughout the specification and appended claims is meant to include not only solutions of the indicated organic compounds, but dispersions and emulsions.

Application of the coatings from the bath can be effected by a variety of methods and includes, but is not limited to, dipping, spraying, electrical deposition, painting and the like. Optionally, the coated substrate can be further treated with an aqueous bath to partially or totally neutralize the free acid. In those instances wherein the substrate is subjected to high temperatures, such as in thermoforming processes, the treatment with the aqueous bath to effect neutralization or partial neutralization is desired.

As indicated above, the hydrophilic lubricious coating of this invention is comprised of at least two components; a polyisocyanate primer and a water-soluble or water dispersible polymer topcoat. They are normally applied in two separate coating steps. However, if desired, the drying step after application of the polyisocyanate coating can be omitted and drying effected after application of the top coat.

The solvents useful for applying the polyisocyanates include methyl ethyl ketone, ethyl acetate, ethyl lactate, chloroform, trichloroethylene, dichloromethane, hexane, heptane, toluene, their mixtures with mineral oil, or other suitable organic solvents which do not react with isocyanates under the coating conditions. The preferred solvent is methyl ethyl ketone.

Alternatively, the polyisocyanates can be dispersed in a solvent/non-solvent mixture to form a dispersion or emulsified to form an oil-in-water emulsion. When an emulsion is used, the reactive isocyanate groups need to be protected by suitable chemical groups known to those skilled in the art.

A wide variety of polyisocyanates can be employed in preparing the coatings of the present invention and include, but are not limited to, toluene-2,3-diisocyanate, toluene-2,6-diisocyanate, commercial mixtures of toluene-2,4- and 2,6-diisocyanates, 4,4'-diphenylmethane diisocyanate, cyclohexylene-1,4-diiisocyanate, m-phenylene diisocyanate, 3,3-diphenyl-4-biphenylene diisocyanate, 4,4-biphenyl diisocyanate, 1,6-hexamethylene diisocyanate, 1,5-naphthalene diisocyanate, cumene-2,3-diisocyanate, 2,4-diisocyanatodiphenylether, 5,6-dimethyl-1.3-phenylenediisocyanate, 2,4-dimethyl-1,3-phenylenediisocyanate, 2,4-dimethyl-1,3-phenylenediisocyanate, 4,4-diisocyanatodiphenylether, 9,10-anthracene diisocyanate, 2,4-diisocyanatotoluene, 1,4-anthracene diisocyanate, 2,4,6-toluene triisocyanate, isophorone diisocyanate, and p,p',p''-triphenylmethane triisocyanate, and the like. Equally useful are isocyanate end-capped prepolymers and adducts, isocyanate end-capped polyfunctional aromatic adducts, isocyanate end-capped polyfunctional aliphatic adduct and two component systems such as end capped aliphatic polyester polyol and aliphatic polyol compound, and their mixtures with different polyisocyanates as described above.

Illustrative of isocyanate end-capped adducts are the reaction products of 2,4-tolylene diisocyanate, 4,4'-diphenylmethane diisocyanate, polymethylenepolyphenyl isocyanate, or 1,5-naphthylene diisocyanate, with 1,2-polypropylene glycol, polytetramethylene ether glycol, 1,4-butanediol, 1,4-butylene glycol, 1,3-butylene glycol, poly(1,4-oxybutylene) glycol, caprolactone, adipic acid esters, phthalic anhydride, ethylene glycol, diethylene glycol, and the like.

The polymers suitable for use in forming the top coatings of the present invention are carboxylic acid-containing polymers. The polymer can be a free acid or partially neutralized as represented by the following formula:

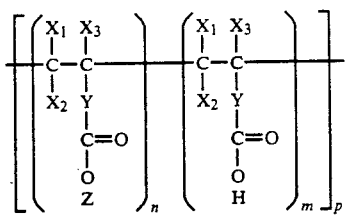

where n=0-0.95 mole fraction of neutralized acid moieties;
m=0.05-1.0 mole fraction of acid moieties with the proviso that n+m=1;
$X_1$, $X_2$, $X_3$ are each a hydrogen atom or a suitable monovalent organic radical, such as lower alkyl or cycloalkyl or aryl of up to 8 carbon atoms, and wherein the X groups are such that the polymer remains water soluble;
Y is either a single bond or any suitable divalent organic radical, such as a hydrocarbon group of up to 8 carbon atoms, provided it does not adversely affect the solubility of the polymer; Z is either a metallic ion or a suitable ammonium ion; and
p is a very large number such that the polymer has a molecular weight between about 200,000 and about 5,000,000.

Even though all poly(carboxylic acid) homopolymers can be useful to different degrees, the high molecular weight polymers are more desirable. The useful molecular weights range from 200,000 to about 5,000,000. Representative carboxylic acid containing homopolymers include, but are not limited to, poly(acrylic acid), poly(methacrylic acid), poly(isocrotinic acid), and the like. the poly(carboxylic acid) of this invention can be either linear or partially cross-linked such that it would form either a solution or a colloidal dispersion in the coating medium. The preferred poly(carboxylic acid) polymer is a poly(acrylic acid) having a molecular weight of from about 200,000 to about 5,000,000. Particularly preferred poly(carboxylic acid) polymers include poly(acrylic acid) polymers having molecular weights of from about 1,000,000 to about 3,000,000.

Olefinic acids such as acrylic acid can be copolymerized with one or more of other unsaturated monomers to produce copolymers containing carboxylic acid moieties. Examplary copolymers include Carboset and SURLYN produced by B.F. Goodrich and DuPont respectively. Copolymers containing water-insoluble units as well as carboxylic acid units can be mixed with the homopolymers if so desired, as long as they are compatible.

Polyampholytes which contain one or more polymeric acids mentioned above may be also useful for the purpose of this invention as long as the basic moiety is a tertiary amine.

Any organic solvents or mixed solvents for the poly(carboxylic acid) polymers used in this invention may be employed for making the topcoat solution provided that they are not reactive with the polyisocyanates. Examplary solvents or solvent mixtures include acetonitrile, acetonitrile-DMF N,N-dimethyl formamide (DMF), acetyl acetone, acrylonitrile, benzonitrile, diethyl acetamide, diethyl formamide, diethylformamide-DMF, dimethyl acetamide, 1,4-dioxane, dipropyl sulfone, DMF-acetone, DMF-toluene, DMSO (dimethyl sulfoxide), DMSO-DMF, ethyl formamide, N-methyl-2-pyrrolidone, nitrobenzene, nitrobenzene-DMF, phehylacetate, propionitrile, styrene, and the like. The dissolution of poly(carboxylic acid) polymers in many of the above-mentioned solvents may be enhance by the addition of suitable amines. The preferred solvent is dimethyl formamide.

To prepare a seed-free poly(carboxylic acid) solution, it is advantageous to add a small amount of surfactant in the solvent before mixing with the polymer. Any soluble surfactant or a mixture of surfactants in the above-mentioned solvents may be useful. The preferred surfactants are soluble nonionic surfactants such as polyoxyethylene sorbitan fatty acid esters, polyoxyethylene acids, polyoxyethylene alcohols, fluorinated alkyl esters, fluorinated alkoxylates and their mixtures.

Due to the high molecular weight of the poly(carboxylic acid) polymers preferred for use in the present invention, their solution viscosities may be too high to be suitable for some coating processes. It is advantages in these instances to convert the polymer solution to a colloidal dispersion by mixing with one or more non-solvents. Exemplary non-solvents include tertiary alcohols, ketones, aliphatic ethers, aliphatic and aromatic hydrocarbons. The preferred non-solvents are acetone, methyethylketone (MEK) and tertiary butyl alcohol.

Alternatively, the poly(carboxylic acid) may be emulsified to a water-in-oil emulsion. an example for forming such a water-in-oil emulsion is described in my earlier U.S. Pat. No. 4,618,647.

For some applications it might be desirable to incorporate one or more additives in the coatings particularly the top coating. For example, some catheters are comprised of a thermoplastic rubber and it is preferred that the primer coating contain a plasticizer to minimize loss of flexibility due to the coating operation. A wide variety of plasticizers can be employed such as the esters of fatty acids, mineral oil or silicone oil. The plasticizer must, of course, be compatible with the components of the coatings and have no undersirable biological properties which would limit their use.

Other additives can be employed in the coatings in addition to the surfactants such as, stabilizers, antioxidants, antimicrobial agents, colorants, biological components and the like. For example, in catheters which are inserted into blood vessels, it may be desirable to have contained in the coating an antithrombogenic agent such as heparin, to avoid blood clot formation during the surgical procedure. The antithrombogenic agent can be used either as an additive or as a chemically bonded moiety of the poly(carboxylic acid) polymer.

The techniques employed in coating the substrates and devices are not necessarily critical and any coating processes suitable for making thin coatings may be utilized. For operations where the shelf-life of the coating solutions is not a critical issue, a single solution system containing a blend of both polyisocyanate and poly(carboxylic acid) may be used in a single coat operation.

In practice it has been found that excellent lubricity and abrasion resistance properties are obtained when the total thickness of the primer and top coating applied to the substrates in accordance with the teachings of this invention is from the submicron range to a few microns.

The concentration of the isocyanate and the carboxylic acid-containing polymer in the respective coating solutions can vary depending upon the particular components employed, their solubility as well as other considerations. In general the polyisocyanate component in the primer coating is contained in the coating solvent in an amount of at least about 0.1% by weight. If the polyisocyanate is in liquid form, it can be employed without a solvent. However, in practice, it is preferred to employ the polyisocyanate in a solvent in a concentration of from about 0.5 to about 20% by weight, and more preferably from about 1 to about 5% by weight.

The amount of the poly(carboxylic acid) component employed in the solvent will be controlled by the viscosity of the medium. Most any concentration can be used as long as it is high enough to permit the preparation of a satisfactory coating, and yet is low enough so that the solution is not too viscous. Concentrations of from about 0.1 to about 10% by weight are preferred with a concentration within the range of about 0.5 to about 2% by weight the most preferred. In practice, the stoichiometry is such that the molar ratio of carboxylic acid groups to isocyanate groups is in excess and will generally be at least about 1:1.

Although the drying temperatures and times are not necessarily critical, it has been found that the coated substrate can be dried at temperatures of from about 20° to about 150° C. and more preferably from about 50° to about 100° C. Drying periods can range from a few seconds to 60 minutes or more.

Many types of catheters need to be thermoformed to specific shapes for their intended applications. Depending on the temperature and length of time of the thermoforming process many coated catheters may lose their hydrophilic lubricity during the thermoforming process. The degree of lubricity loss depends on the severity of the thermoforming conditions.

Thus, when the temperatures are sufficiently high lubricity may be decreased due to the cyclization of adjacent acid groups. Accordingly, it is preferred to neutralize or partially neutralize the acid groups to prevent such cyclization. The description of treatment of the acid groups by sodium phosphates and preferred formulations are set forth in the examples.

The hydrophilic lubricious coatings of this invention are useful in coating medical devices, where a slippery exterior and/or interior, are necessary or desirable to minimize injury to tissues and to aid in manipulation of the devices during surgical procedures. Examplary medical devices include catheters, needles, guide wires, prophylactic devices, delivery systems, filters, sheaths, and other accessories employed in medical diagnostics, drainage, dilatation occlusion, vena cava and the like. While the invention is particularly applicable to medical devices, it can also be used to coat a variety of other substrates. for instance, the coatings can be applied to condoms, skis, toboggans, and those instances wherein a lubricious surface is desired.

In the examples which follow, certain abbreviations have been employed to define the various polyisocyanates and poly(carboxylic acids). All of the compounds are readily available from commercial sources.

| Polyisocyanate | Composition |
|---|---|
| A- | 1,6-diisocyanatohexane |
| B- | 2,4-toluene diisocyanate |
| D- | An isocyanate end-capped aliphatic prepolymer having an average NCO equivalent weight of 350 and a solution viscosity of about 1,000 cps at 25° C. |
| E- | An aromatic isocyanate end-capped pre- |

| | polymer average NCO equivalent weight 182. |
|---|---|
| Poly(carboxylic acid) | Composition |
| L- | A poly(acrylic acid) partially cross-linked homopolymer having a molecular weight of about 3,000,000. |
| M- | A USP grade poly(acrylic acid) partially cross-linked homopolymer having a molecular weight of about 3,000,000. |
| N- | A poly(acrylic acid) homopolymer having a molecular weight of about 1,250,000. |

The following examples are illustrative of the invention:

EXAMPLE 1

A nylon 6 coupon was compression molded from CAPRON 8000 (Allied Chemicals). The coupon was first dipped into a 1% solution of 1,6-diisocyanatohexane (A) in methyl ethyl ketone (MEK) for one hour. The coupon was subsequently removed from the MEK bath and dried in a 60° C. air oven for 30 minutes. The dried coupon was then dipped in a 1% solution of poly(acrylic acid) (L) in dimethylsulfoxide (DMSO) for one second. It was redried at 60° C. air oven for 30 minutes. The finished coating was smooth, non-tacky, as well as easy to handle. It became instantly slippery upon exposure to water.

EXAMPLE 2

The coated nylon 6 coupon was soaked in a water bath for three hours at room temperature. The soaked coupon retained a high degree of lubricity. This experiment shows that the poly(acrylic acid) coating was held tightly onto the nylon 6 substrate and was not leached out during the soaking.

EXAMPLE 3

A nylon 11 coupon was compression molded from RISAN BESNO-545344. The coupon was treated according to the same procedure described in Example 1. The finished coating on the nylon 11 coupon became lubricious instantly upon exposure to water.

EXAMPLE 4

The coated nylon 11 coupon was soaked in a water bath for three hours at room temperature. The soaked nylon 11 coupon remained to be highly lubricious. This experiment illustrates that the poly(acrylic acid) coating was not dissolved away during the soaking.

EXAMPLE 5

Example 1 was repeated with the exception that N,N-dimethyl formamide (DMF) was substituted for DMSO as the solvent for the poly(acrylic acid). A very lubricious coating was obtained when exposed to water.

EXAMPLE 6

Example 5 was repeated with the exception that the concentration of the poly(acrylic acid) was 0.5 instead of 1%. The finished coating was slightly more smooth and become lubricious upon exposure to water.

EXAMPLE 7

Example 6 was repeated with the exception that (1) an 0.2% poly(acrylic acid) solution was used and (2) the acid polymer was partially neutralized by adding 50% stoichiometric amount of triethylamine. A smooth coating was obtained which became lubricious upon exposure to water.

EXAMPLE 8

A nylon 11 coupon was compression molded from bismuth carbonate filled nylon 11 pellets. The coupon was coated in a 1% solution of toluene 2,4-diisocyanate (B) in MEK for one hour. After drying in an air oven at 60° C. for 30 minutes, the coupon was dipped in a 1% solution of poly(acrylic acid) (L) in dimethylformamide (DMF). After redrying at 60° C. for 30 minutes, a smooth coating was obtained. The surface of the coupon became lubricious instantly upon exposure to water.

EXAMPLE 9

A surgical catheter made of bismuth carbonate filled nylon 11 was coated by the same procedure as described in Example 8 with the exception that poly(acrylic acid) (M) was substituted for (L). The finished catheter had a continuous, smooth coating which became very lubricious upon exposure to water.

EXAMPLE 10

(a) Example 9 was repeated with the exception that a 1% solution of a (vinyl methyl ether-maleic anhydride) copolymer (GANTREZ-AN 169 produced by GAF) in MEK was substituted for the poly(acrylic acid) solution as the topcoat. The freshly prepared coating showed no lubricity upon exposure to water. It became lubricious, however, after overnight soaking in a water bath. This example illustrates a deficiency of the prior technique described in European patent application 0166998.

(b) A nylon 11 catheter was coated by dipping in a 1% DMF solution of polyisocyanate (B) for 1 hour after which it was dried at 60° C. for one hour. the catheter was then dipped in a 1% DMF solution of polyvinyl hydrophthalate for 1 second and dried 30 minutes at 60° C. Upon dipping in water there was no development of a lubricious coating.

EXAMPLE 11

Example 9 was repeated with the exception that 1,6-diisocyanatohexane (A) was substituted for toluene 2,4-diisocyanate (B) in the primer solution. A smooth coating was obtained which became slippery instantly upon exposure to water.

EXAMPLE 12

Example 9 was repeated with the exception that an isocyanate end capped polyfunctional aliphatic adduct (D) was substituted for toluene diisocyanate. The isocyanate solution was made of 2.03 grams of (D) and 150 grams of MEK which corresponded to an 0.8% solids solution. The finished coating was continuous and smooth, which developed lubricity immediately upon exposure to water.

EXAMPLE 13

Example 12 was repeated with the exception that an (ethylene-vinyl acetate) copolymer catheter was substituted for the nylon 11 catheter. The coated catheter showed no discoloration and was smooth. It developed lubricity instantly upon exposure to water.

EXAMPLE 14

A section of the coated catheter prepared in example 12 was examined for lubricity retention in a saline solution (0.5% NaCl). The following observations were noted and are set forth in Table I below:

TABLE I

| Soaking time, hours | Observation |
| --- | --- |
| 1/6 | remained lubricious |
| ½ | remained lubricious |
| 1 | remained lubricious |
| 24 | remained lubricious |
| After redrying at 60° C. | normal feel |
| Exposed to saline again | remained lubricious |

These results demonstrate that the hydrophilic lubricious coating of this invention is resistant to saline.

EXAMPLE 15

Two coated nylon 11 catheters, one taken from example 9 and the other from example 12, were immersed in a hot water bath at 70° C. and examined for any loss of lubricity. The results obtained are set forth in Table II below:

TABLE II

| Time in 70° C. Bath, hours | Observation |
| --- | --- |
| 0 | lubricious |
| 1 | lubricious |
| 2 | lubricious |
| 3 | lubricious |
| 4 | lubricious |

It is evident from the above data that the coating of the present invention demonstrated a good retention of lubricity in hot water at 70° C.

EXAMPLE 16

This example illustrates a preferred method for making a uniform low-viscosity solution (or colloidal dispersion) of poly(acrylic acid) (M) in DMF or similar solvents. Such a solution is easier to handle, filters more rapidly and results in a more uniform coating.

A total of 180 grams of DMF and 0.09 grams of TWEEN 80 [poly(oxyethylene) (20) Sorbitan monooleate, a non-inoic surfactant supplied by ICI] were placed in a 500 ml beaker. The mixture was blended for 5 minutes using an air-driven Cowless mixer. Thereafter, 1.8 grams of (M) was sprinkled into the liquid while under mixing. The mixing was continued for a total of 15 minutes. A highly uniform, gel-seeds-free solution (colloidal dispersion) was obtained, the finished solution exhibited a Brookfield viscosity (Model LVT, 6 RPM at 25° C.) of 55 cps. The dissolution process was much more time-consuming without the surfactant, and the finished solution typically exhibited a viscosity of about 100 cps.

EXAMPLE 17

EXAMPLE 16 was repeated with the exception that BRIJ 98 [polyoxyethylene (20) oleylether, a non-ionic surfactant produced by ICI] was substituted for the Tween 80. A uniform gel-seed-free solution (colloidal dispersion) was obtained. The solution filtered through a 16 micron filter with ease. The finished solution exhibited a Brookfield viscosity of 45 cps.

EXAMPLE 18

Example 17 was repeated with the exception that MYRJ 53 (polyoxyethylene (50) stearate, a non-inoic surfactant produced by ICI) was substituted for BRIJ 98. A uniform, gel-seed-free solution (colloidal dispersion) was obtained. The solution filtered through a 16 micron filter with ease. The finished solution exhibited a Brookfield viscosity of 45 cps (Model LTV, 6 rmp at 25° C.).

EXAMPLE 19

A stainless steel guide wire made by Medi-tech was coated with a primer solution composed of 1% polyisocyanate (D) in MEK and a topcoat solution composed of 1% poly(acrylic acid) (M) and 0.05% of MYRJ 53 (surfactant) in DMF. The drying cycles used for the two coats were 30 minutes at 70° C. and 30 minutes at 60° C., respectively. The finished stainless steel guide wire showed a lubricious surface upon exposure to water.

EXAMPLE 20

A bismuth carbonate filled nylon 11 catheter was first dipped in a 1% tolylene-2,4-diioscyanate solution in MEK for one hour. The catheter was removed from the bath and dried in an air oven at 90° C. for 30 minutes. It was dipped-coated in a poly(acrylic acid) (M) bath having a formulation identical to that of example 18 for 1 second. The catheter was redried at 90° C. for 30 minutes. The finished coating was very lubricious and showed a high degree of abrasion resistance.

EXAMPLE 21

A nylon 11 catheter was coated by first treating in a primer solution containing 0.5% and 0.5% of polyiscyanate (D) and tolylene 2,4-diisocyanate, respectively. The catheter was dried at 85° C. for 30 minutes and subsequently dipped in a 1% poly(acrylic acid) (L) solution for one second. It was then redried at 85° C. for 30 minutes. The finished catheter was smooth, and showed a high degree of lubricity upon exposure to water. The hydrophilic lubricious coating on this catheter was resistant to abrasion, and retained much of its initial lubricity after rubbing with a wet tissue ten times.

EXAMPLE 22

A nylon 11 catheter was coated according to the same procedure described in example 21 with the exception that the ratio of tolylene 2,4-diisocyanate to (D) was changed from 0.5/0.5 to 0.75/0.25. The finished catheter was very lubricious upon exposure to water. It exhibited good abrasion resistance as measured by the rub test described in example 21.

EXAMPLE 23

A catheter was coated according to the procedure of example 22 with the exception that the drying temperature was 60 instead of 85° C. The finished catheter was very lubricious upon exposure to water.

EXAMPLE 24

A double-coating procedure is illustrated in this example. Five pieces of nylon 11 catheters were first soaked in a 1% tolylene 2,4-diisocyanate solution in MEK for one hour. After 30 minutes drying in an air oven at 85° C., they were dipped-coated in a 1% poly(acrylic acid) (M) bath for one second. They were redried at 85° C. for 30 minutes. The above coating procedure was repeated once more with the exception that the dipping time in the primer solution was shortened from one hour to 10 minutes for the second coating. The finished catheters were very slippery upon exposure to water.

EXAMPLE 25

A low viscosity, uniform colloidal dispersion of poly(acrylic acid) (N) [a high molecular weight linear poly(acrylic acid)] was prepared by the following procedure: Ten grams of (N) were added under mixing with a Cowless air mixer to a solution containing 0.5 grams of MYRJ 53 surfactant and 659.7 grams of DMF. A viscous solution was obtained in about 15 minutes. Thereafter, 32.98 grams of MEK were added into the solution under mixing to yield a slightly cloudy colloidal dispersion. The colloidal dispersion possessed a Brookfield viscosity (Model LVT, 6 rpm at 25° C.) of 162cps. Without MEK, a 1% (N) in DMF would produce a viscosity of 2,300 cps.

EXAMPLE 26

A nylon 11 catheter was coated using the procedure described in example 21 with the exception that the primer solution was a 1% tolylene 2,4-diisocyanate solution in MEK and the top coat solution was a 1% poly(acrylic acid) (N) in DMF prepared in accordance with example 24. The finished coating was very smooth and became lubricious instantly upon exposure to water.

EXAMPLE 27

A bismuth carbonate filled nylon 11 catheter was coated with a hydrophilic lubricious coating by the following procedure:
(1) Dipped in an 1% tolylene 2,4-diisocyanate solution in MEK for one hour.
(2) Dried in an air oven at 85° C. for 30 minutes.
(3) Dipped in a 1% poly(acrylic acid) ((L) solution for one second.
(4) Dried in an air oven at 85° C. for 30 minutes.
(5) Repeated (1) except for 10 minutes.
(6) Repeated (2).
(7) Repeated (3).
(8) Repeated (4).

The finished coating was smooth and continuous. It became very slippery instantly upon exposure to water and showed a good abrasion resistance by the tissue paper rub test.

EXAMPLE 28

Example 27 was repeated with the exception that a nylon 12 catheter was substituted for the nylon 11 catheter. The finished coating was lubricious and exhibited good abrasion resistance.

EXAMPLE 29

A catheter made of thermal plastic rubber Kraton was coated according to the following procedure:
(1) Dipped in a bath containing a primer solution of the following composition

| Tolylene diisocyanate | 0.75% |
|---|---|
| Isocyanate (D) | 0.25% |
| Mineral Oil | 15% |

| -continued | |
|---|---|
| DMF | 84% | for one minute duration.
(2) Dried in an air oven at 85° C. for 30 minutes.
(3) Dipped in a 1.5% poly(acrylic acid) (M) solution in DMF for one second.
(4) Dried in an air oven at 85° C. for 30 minutes.

The finished catheter retained its flexibility, showed negligible shrinkage, and a smooth coating. The latter became very lubricious upon exposure to water and was resistant to abrasion.

EXAMPLE 30

A catheter made of poly(ethylene vinyl acetate) was coated according to the following procedure:
(1) Dipped in a 1% isocyanate (D) solution in MEK for 30 minutes.
(2) Dried at 60° C. for 30 minutes.
(3) Dipped in a 1.5% poly(acrylic acid) (M) solution in DMF for one second.
(4) Dried at 60° C. for 30 minutes.
(5) Repeated (1) but for 10 minutes.
(6) Repeated (2).
(7) Repeated (3).
(8) repeated (4).

The finished catheter was very smooth and retained its original whitish color. It became lubricious instantly upon exposure to water. The coating was practically unaffected after 10 rubs with a wet tissue paper.

EXAMPLE 31

A 6-inch tip of a guide catheter wire used in conjunction with a catheter was coated using the procedure described in the previous examples. The guide wire was dipped in a primer solution containing 1.0% isocyanate (D in MEK and dried for 10 minutes at 85° C. The wire was subsequently dipped in a 1.5% poly(acrylic acid) (M) solution in DMF for 1 second and redried. The coated guide wire showed a good degree of lubricity and retained much of its initial lubricity after rubbing with a wet tissue 4 times.

EXAMPLE 32

Example 31 was repeated on the full length of the guide wire using a 7:3 DMF/MEK solvent for the poly(acrylic acid) and the sequence of coating was repeated a second time. the coated guide wire exhibited a good degree of lubricity upon exposure to water.

EXAMPLE 33

The full length of a nylon 11 catheter comprised of a polyether thermoplastic elastomer and fitted with a polyethylene terephthalate balloon was coated in a manner similar to the preceding examples. The catheter including the balloon were dipped in a primer solution containing 1% isocyanate (D) in MEK and dried for 30 minutes at 85° C. The catheter with balloon were subsequently dipped in a 1.5% poly(acrylic acid) (L) dispersion (7:3 DMF/MEK) for 1 second and dried. The catheter showed very good lubricity upon exposure to water and retained much of initial lubricity after rubbing 8 times with a wet tissue.

EXAMPLE 34

An experiment was conducted to demonstrate the preparation of catheters having hydrophilic lubricious coatings from a blend of a polyisocyanate and a carboxylic acid-containing polymer. A dispersion was prepared containing 98 grams of poly(acrylic acid) (M), 0.3 grams of MYRJ53 surfactant, 157.5 grams of MEK, and 433.18 grams of DMF. This dispersion had a Brookfield viscosity of 40 cps. Into 196.67 grams of this dispersion was added 3.33 grams of isocyanate (D) and the blend stirred for 10 minutes. Two nylon 11 catheters were dipped into this blend, the first for 1 minute and the second for 10 minutes. Both catheters were dried for 30 minutes at 85° C. Both catheters were not slippery when dry, but upon exposure to water, they exhibited good lubricity. The catheters also exhibited fairly good abrasion after 9 and 12 rubs respectively by the tissue rub test.

EXAMPLES 35-58

Additional experiments were conducted to evaluate various catheters coated in accordance with the present invention and wherein variations were made in coating compositions, solvents, number of coatings, drying times and the like. The pertinent data is set forth in Tables I-III below:

TABLE I

PREPARATION AND EVALUATION OF ETHYLENE VINYL ACETATE COPOLYMER CATHETER

| | Primer Coating[2] | | | Top Coating[3] | | | Evaluation | |
|---|---|---|---|---|---|---|---|---|
| Example[1] | Isocyanate | Weight (%) | Solvent | Acid Compound | Weight % | Solvent* | Abrasion | lubricity |
| 35 | 2,4-TDI | 0.5 | MEK | (M) | 1.0 | DMF | good | good |
|  | (D) | 0.5 |  |  |  |  |  |  |
| 36 | (D) | 1.0 | MEK | (M) | 1.0 | DMF | good | good |
| 37 | TDI | 0.25 | MEK | (M) | 1.0 | DMF | good | good |
|  | (D) | 0.75 |  |  |  |  |  |  |
| 38 | 2,4-TDI | 0.75 | MEK | (M) | 1.0 | DMF | good | good |
|  | (D) | 0.25 |  |  |  |  |  |  |
| 39 | 2,4-TDI | 0.75 | MEK | (M) | 0.75 | DMF | good | good |
|  | (D) | 0.25 |  |  | 0.25 |  |  |  |
| 40** | (D) | 1.0 | MEK | (N) | 1.0 | DMF | good | good |
| 41** | (D) | 1.0 | MEK | (M) | 1.0 | DMF | good | good |
| 42 | (D) | 1.0 | MEK | (M) | 1.0 | DMF | good | good |

[1]The ethylene vinyl acetate catheters were 4 inches in length.
[2]The catheters were soaked for 60 minutes and dried at 65° C.
[3]The catheters were dipped for 1 second and dried at 65° C.
*Also contained MYRJ53 surfactant.
**Entire catheter coated and coating sequence repeated.

TABLE II
PREPARATION AND EVALUATION OF FLEXIBLE THERMOPLASTIC RUBBER CATHETER

| Example[1] | Catheter Size | Primer Coating[2] Isocyanate | Weight (%) | Solvent | Top Coating[3] Acid Compound | Weight % | Solvent | Evaluation Abrasion | lubricity |
|---|---|---|---|---|---|---|---|---|---|
| 43 | 4" | 2,4-TDI (D) | 0.75 0.25 | MEK | (M) | 1.5 | DMF/MEK (7:3) | 18 (rubs) | good |
| 44 | 12" | TDI (D) | 0.75 0.25 | MEK | (M) | 1.5 | DMF/MEK (7:3) | 18 | good |
| 45 | 12" | TDI (D) | 0.75 0.25 | MEK | (M) | 1.5 | DMF/MEK (7:3) | 21 | good |
| 46 | 12" | 2,4-TDI (D) | 0.75 0.25 | MEK | (M) | 1.5 | DMF/MEK (1:1) | 9 | good |
| 47* | full | (D) | 1.05 | MEK | (M) | 1.0 | DMF | 20 | good |
| 48 | 4" | (D) | 1.0 | MEK | (M) | 1.0 | DMF | 10 | good |
| 49 | half | (D) | 1.0 | MEK | (M) | 1.0 | DMF | 10 | good |
| 50* | half | (D) | 1.0 | MEK | (M) | 1.0 | DMF | 12 | good |

[1]examples 43–46 and 50 used mineral oil in MEK.
[2]The catheters were soaked for 60 minutes and dried at 65° C.
[3]The catheters were dipped for 1 second and dried at 65° C.
*Entire catheter coated and coating sequence repeated.

TABLE III
PREPARATION AND EVALUATION OF NYLON 11 CATHETERS

| Example[1] | Catheter Size | Primer Coating[2] Isocyanate | Weight (%) | Solvent | Top Coating[3] Acid Compound | Weight % | Solvent | Evaluation Abrasion | lubricity |
|---|---|---|---|---|---|---|---|---|---|
| 51 | 4" | TDI | 1.0 | MEK | (M) | 1.5 | DMF/MEK (7:3) | 15 (rubs) | good |
| 52* | 4" | TDI | 1.0 | MEK | (M) | 1.5 | DMF/MEK (7:3) | 40 | good |
| 53* | 12" | TDI | 1.0 | MEK | (M) | 1.0 | Dioane | 15 | very good |
| 54 | 12" | TDI | 1.0 | MEK | (M) | 1.0 | Dioxane | 10 | very good |
| 55* | 12" | TDI | 1.0 | MEK | (M) | 1.0 | DMF | 35 | very good |
| 56* | 12" | TDI | 1.0 | MEK | (M) | 1.0 | DMF/MEK (7:3) | 20 | very good |
| 57 | 12" | TDI | 1.0 | MEK | (M) | 1.0 | DMF | 30 | very good |
| 58 | 12" | TDI | 1.0 | MEK | (M) | 1.0 | DMF/MEK (7:3) | 15 | very good |

[1]Examples 57 and 58 were Nylon 12 catheters.
[2]The catheters were soaked for 60 minutes and dried at 85° C. except for Example 56 which soaked for 30 minutes.
[3]The catheters were dipped for 1 second and dried at 85° C.
*Coating sequence repeated with 60 minute primer soak and 10 minute top coat soak.

EXAMPLE 59

A low viscosity, uniform colloidal dispersion of poly(acrylic acid) (N) was prepared by the following procedure: Into a 2-liter stainless steel reactor, equipped with a turbine agitator, condenser, thermometer, and an exterior heating bath, there was charged under agitation 487.17 grams of DMF (Mallinckrodt), 252.7 grams of MEK (Mallinckrodt), 234.3 grams of tertiary butyl alcohol (Arco), and 0.83 grams of MYRJ-53 (an ethoxylated steric acid produced by ICI). Once a uniform solution was obtained, 25 grams of poly(acrylic acid) (N) powder were introduced by pouring directly into the reator, The reactor was heated to 50° C. and maintained at 50±2° C. for one hour while under agitation at 2000 rpm. Thereafter, the reactor was cooled to room temperature and the content was transferred into a Waring Blender for homongenization. The homogenized product was filtered through a 10 micron polypropylene filter cartridge to yield a uniform colloidal dispersion. It showed the following viscosity properties:

| Before homogenization | |
|---|---|
| Brookfield viscosity | 40 centipoises |
| Kinematic viscosity | 17.3 centistokes |

| After homogenization | |
|---|---|
| Brookfield viscosity | 7 censtpoises |
| Kinematic viscosity | 8.7 centistokes |

EXAMPLE 60

A primer solution was prepared by mixing 80.91 parts of MEK (Mallinckrodt), 15.47 parts of mineral oil (Malincrodt), 3.6 parts of polyisocyanate E and 0.02 parts of FLUORAD 431 ( a surfactant produced by 3M) to yield a mobil, clear liquid. The solution contained 0.84% by weight of isocyanate groups.

EXAMPLE 61

This example illustrates the preparation of a sodium phosphate solution for the acid neutralization of the poly(carboxylic acid) coating of this invention.

An 0.1N sodium phosphate solution was prepared by dissolving 13.8 grams of the reagent (Matheson, Coleman & Bell) into one liter of distilled water. Separately, an 0.1N disodium phosphate solution was made by mixing 7.1 grams of the reagent (Matheson, Coleman & Bell) into one liter of distilled water. Into a one liter beaker containing about 660 ml of the 0.1N disodium phosphate solution, there was added under mixing a sufficient amount of the 0.1N sodium phosphate solution until pH reached 7.

EXAMPLE 62

A plasticized styrene-butadiene catheter was coated according to the following process to yield durable lubricious coating of this invention.

A 15 inch long, catheter was dipped for 1 minute in a stainless steel bath containing the primer of Example 60. The coated catheter was air dried briefly and followed by baking in a forced air oven at 85° C. for 30 minutes. The primed catheter was dipped quickly in a topcoat bath containing the polyacrylic acid colloidal dispersion of Example 59. following a brief air-drying the wet catheter was dried in the oven at 85° C. for 60 minutes. A uniform coating was produced, which became lubricious instantly upon exposure to water. The coating exhibited a good adhesion to the catheter.

EXAMPLE 63

This example illustrates the utility of post neutralization for preserving hydrophilic lubricity of the coated catheter during a thermoforming process.

A plasticized polystyrene-butadiene catheter coated according to Example 62 was dipped in a bath containing the sodium phosphate solution of Example 61. The treated catheter was air dried for one hour. thereafter the catheter was shaped and heated in that shape at 120° C. for 90 minutes. The finished shaped catheter became lubricious instantly upon exposure to water.

EXAMPLE 64

The thermoforming treatment of Example 63 was repeated without first dipping in the sodium phosphate solution. The finished stem was no longer lubricious upon exposure to water.

EXAMPLE 65

This example illustrates the preparative procedure for producing a top coat solution containing a poly(methacrylic acid) polymer.

Into a one-liter size Pyrex glass reactor equipped with a turbine agitator, a thermometer, a condenser, an external heating bath and an addition funnel there was charged 312 grams of DMF, 120 grams of t-butyl alcohol, 158.7 grams of MEK, 0.3 grams of MYRJ-53 surfactant and 9 grams of poly(methacrylic acid) (Polysciences). The mixture was heated to 50° C. while under vigorous mixing. After 1 hour mixing, a uniform solution was obtained. The solution was cooled to room temperature and its solution viscosity measured with a Brookfield Model LVT Viscometer. The value was 5 centipoises.

EXAMPLE 66

The same thermoplastic rubber catheter used in Example 43 was coated with the polyisocyanate primer (E) and the poly(methacrylic acid) top coat solution prepared in Example 65 according to the following procedure:
1. One minute dip in the primer solution.
2. One minute air dry and followed by a 30 minute bake in a 85° C. forced-air oven.
3. One second dip in the poly(methacrylic acid) top coat solution.
4. One minute air drain and followed by a 60 minute bake in a 85° C. forced-air oven.

The finished catheter was lubricious upon contacting with water.

EXAMPLE 67

Example 66 was repeated with the exception that a Nylon 11 catheter was used instead of the thermoplastic rubber catheter. The coated catheter was lubricious upon contact with water.

EXAMPLE 68

This example illustrates the utility of a spray coating process for producing the lubricious coating of the invention. a group of four thermoplastic rubber catheters were cut to a length of 18 inches and mounted on steel mandrels. The latter were mounted on a steel stand inside a ventilated hood. The polyisocyanate primer (E) was sprayed onto the catheters using an air-spray gun(-the Devilbiss Co., Toledo, Ohio, Type JGA-502). After a 30 minute baking at 85° C. in a forced-air oven, the primed catheters were sprayed with a coat of poly(methacrylic acid) top coat (N). After a 60 minute baking, a fairly smooth coating was obtained. the coated catheters became lubricious immediately upon exposure to water.

Although the invention has been illustrated by the preceding examples, it is not to be construed as being limited to the materials employed therein, but rather, the invention relates to the generic area as herein before disclosed. Various modifications and embodiments thereof can be made without departing from the spirit or scope thereof.

I claim:

1. A method of covering at least a portion of a substrate with a hydrophilic coating which coating exhibits good abrasion resistance and an increased lubricity when contacted with an aqueous-containing fluid, said method comprising the steps of:
   (1) contacting said substrate with polyisocyanate contained in at least one first inert solvent to provide at least a partially coated substrate;
   (2) contacting said coated substrate with a poly(acrylic acid) polymer of the formula:

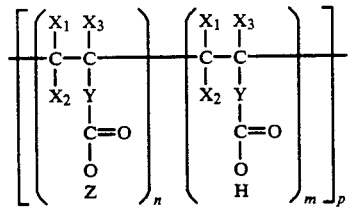

where
$n = 0$–$0.95$ mole fraction of neutralized acid moieties,
$m = 0.05$–$1.0$ mole fraction of acid moieties with the proviso that $n + m = 1$,
$X_1$, $X_2$, $X_3$ are each a hydrogen atom or a monovalent organic radical,
$Y$ is a single bond or a divalent organic radical,
$Z$ is a metallic ion or a tertiary ammonium ion, and
$p$ is a number such that the polymer has a molecular weight between about 200,000 and about 5,000,000, said poly(acrylic acid) polymer contained in at least one second solvent to provide a multiple coated substrate; and (3) thereafter drying said multiple coated substrate to provide a hydrophillic, lubricious coating which contains free carboxylic acid groups or partially neutralized carboxylic acid groups.

2. The method of claim 1 wherein said substrate is a medical device.

3. The method of claim 2 wherein said medical device is a catheter.

4. The method of claim 1 wherein said substrate coated with said polyisocyanate is dried at a temperature of up to about 150° C. before step (2).

5. The method of claim 4 wherein said multiple coated substrate is dried at a temperature of from about 25° to about 150° C.

6. The method of claim 1 wherein said first solvent is methyl ethyl ketone.

7. The method of claim 1 wherein said first solvent is ethyl acetate.

8. The method of claim 1 wherein said first solvent is a mixture of at least two solvents.

9. The method of claim 8 wherein said mixture contains mineral oil.

10. The method of claim 8 wherein said mixture contains at least one surfactant.

11. The method of claim 1 wherein said second solvent is at least one organic solvent inert to said poly(acrylic acid) polymer.

12. The method of claim 1 wherein said second solvent is dimethylformamide.

13. The method of claim 1 wherein said second solvent is dimethylsulfoxide.

14. The method of claim 1 wherein said second solvent is a mixture of dimethylformamide and methyl ethyl ketone.

15. The method of claim 1 wherein said second solvent is a mixture of dimethylformamide, methyl ethyl ketone and t-butyl alcohol.

16. The method of claim 1 wherein said polyisocyanate is a diisocyanate.

17. The method of claim 16 wherein said diisocyanate is a mixture of toluene 2,4- and 2,6-diisocyanate.

18. The method of claim 16 wherein said diisocyanate is a diphenylmethane diisocyanate.

19. The method of claim 16 wherein said diisocyanate is an adduct of diphenylmethane diisocyanate and a polyol.

20. The method of claim 1 wherein said polyisocyanate is an isocyanate end-capped polyfunctional aliphatic adduct.

21. The method of claim 1 wherein said polyisocyanate is an isocyanate end-capped polyfunctional aromatic adduct.

22. The method of claim 1 wherein said coated substrate is thermoformed to different shapes.

23. The method of claim 22 wherein said coated substrate is first treated with an alkaline bath before thermoforming.

24. The method of claim 22 wherein said coated substrate is first treated with an alkali metal salt bath before thermoforming.

25. The method of claim 22 wherein said coated substrate is first treated with an alkali metal phosphate bath before thermoforming.

26. The method of claim 1 wherein said polyisocyanate is a reaction product of a polyfunctional isocyanate with an aliphatic polyester polyol.

27. The method of claim 1 wherein said polyisocyanate is a reaction product of a polyfunctional isocyanate with an aromatic polyester polyol.

28. The method of claim 1 wherein said polyisocyanate is a mixture of a diisocyanate and an isocyanate end-capped polyfunctional adduct.

29. The method of claim 1 wherein said poly(acrylic acid) polymer is a colloidal dispersion of a homopolymer.

30. The method of claim 1 wherein said poly(acrylic acid) polymer has a molecular weight of from about 200,000 to about 5,000,000.

31. The method of claim 30 wherein said poly(acrylic acid) polymer has a molecular weight of about 3,000,000.

32. The method of claim 1 wherein said carboxylic acid-containing polymer is a copolymer.

33. The method of claim 1 wherein said carboxylic acid containing polymer is partially cross-linked, and contains at least some water insoluble units.

34. The method of claim 1 wherein said polyisocyanate applied as a dispersion.

35. The method of claim 1 wherein said poly(isocyanate) is applied as an oil-in-water emulsion.

36. The method of claim 1 wherein said poly(acrylic acid) polymer is applied as an emulsion.

37. The method of claim 1 wherein said poly(acrylic acid) polymer is applied as a dispersion.

38. A method of covering at least a portion of a substrate with a hydrophilic coating having good abrasion resistance, and which exhibits an increased lubricity when contacted with an aqueous-containing fluid, said method comprising the steps of:

(1) contacting said substrate with a polyisocyanate contained in at least one first inert organic solvent to provide at least a partially coated substrate;

(2) contacting said coated substrate with a poly(acrylic acid) polymer of the formula:

$$\left[ \left( \begin{array}{c} X_1 \; X_3 \\ | \quad | \\ -C-C- \\ | \quad | \\ X_2 \; Y \\ | \\ C=O \\ | \\ O \\ | \\ Z \end{array} \right)_n \left( \begin{array}{c} X_1 \; X_3 \\ | \quad | \\ -C-C- \\ | \quad | \\ X_2 \; Y \\ | \\ C=O \\ | \\ O \\ | \\ H \end{array} \right)_m \right]_p$$

where $n = 0$–$0.95$ mole fraction of neutralized acid moieties;

$m = 0.05$–$1.0$ mole fraction of acid moieties with the proviso that $n + m = 1$;

$X_1, X_2, X_3$ are each a hydrogen atom or a monovalent organic radical;

Y is a single bond or a divalent organic radical;

Z is a metallic ion or a tertiary ammonium ion; and p is a number such that the polymer has a molecular weight between about 200,000 and about 5,000,000;

said carboxylic acid-containing polymer contained in at least one second inert organic solvent to provide a multiple coated substrate; and (3) thereafter drying said multiple coated substrate to provide a hydrophilic, lubricious coating.

39. The method of claim 38 wherein the first solvent is methyl ethyl ketone.

40. The method of claim 38 wherein the second solvent is dimethylformamide.

41. The method of claim 38 wherein said second solvent is a mixture of dimethylformamide and methyl ethyl ketone.

42. The method of claim 38 wherein said substrate coated with said polyisocyanate is dried at a temperature of up to about 150° C. before step (2).

43. The method of claim 38 wherein at least one of said first or second solvents contains a surfactant.

44. The method of claim 1 wherein at least one additive is incorporated into said coating.

45. The method of claim 38 wherein at least one additive is incorporated into said coating.

46. The method of claim 44 wherein said additive is an antithrombogenic.

47. The method of claim 44 wherein said additive is heparin.

48. A method of covering at least a portion of a substrate with a hydrophilic coating which coating exhibits good abrasion resistance and an increased lubricity when contacted with an aqueous-containing fluid, said method comprising the steps of:
(1) contacting said substrate with polyisocyanate contained in at least one first inert solvent to provide at least a partially coated substrate;
(2) drying said coated substrate to provide a primer coat of the polyisocyanate on the substrate;
(3) contacting said coated substrate with a poly(acrylic acid) polymer of the formula:

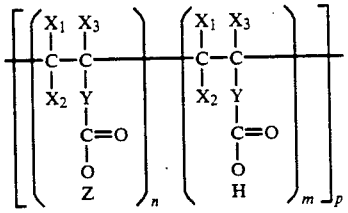

where
$n = 0$–$0.95$ mole fraction of neutralized acid moieties,
$m = 0.05$–$1.0$ mole fraction of acid moieties with the proviso that $n + m = 1$,
$X_1$, $X_2$, $X_3$ are each a hydrogen atom or a monovalent organic radical,
Y is a single bond or a divalent organic radical,
Z is a metallic ion or a tertiary ammonium ion, and
p is a number such that the polymer has a molecular weight between about 200,000 and about 5,000,000, said poly(acrylic acid) polymer contained in at least one second solvent to provide a multiple coated substrate;
(4) thereafter drying said multiple coated substrate to provide a hydrophillic, lubricious coating which contains free carboxylic acid groups or partially neutralized carboxylic acid groups; and
(5) optionally neutralizing the multiple coated substrate.

49. The method of claim 48 wherein the polyisocyanate is diphenylmethane diisocyanate or an adduct thereof, wherein the first inert solvent is either methyl ethyl ketone or toluene, wherein the second inert solvent is a mixture of methyl ethyl ketone, dimethylformamide and t-butyl alcohol.

50. The method of claim 49 wherein the polyisocyanate is diphenylmethane dioscyanate or an adduct thereof in the first inert solvent is present in a concentration of from about 0.5 to about 20 percent by weight and the poly(acrylic acid) in the second inert solvent is present in a concentration of from about 0.1 to about 10 percent by weight.

51. The method of claim 50 wherein the polyisocyanate is diphenylmethane diisocyanate or an adduct thereof in the first inert solvent is present in a concentration of from about 1 to about 5 percent by weight and the poly(acrylic acid) in the second inert solvent is present in a concentration of from about 0.5 to about 2 percent by weight.

52. The method of claim 48 wherein the polyisocyanate is a mixture of different polyisocyanates, wherein the first inert solvent is either methyl ethyl ketone or toluene, wherein the second inert solvent is a mixture of methyl ethyl ketone, dimethylformamide and t-butyl alcohol.

* * * * *

UNITED STATES PATENT AND TRADEMARK OFFICE
CERTIFICATE OF CORRECTION

PATENT NO. : 5,091,205

DATED : February 25, 1992

INVENTOR(S) : You-Ling Fan

It is certified that error appears in the above-identified patent and that said Letters Patent is hereby corrected as shown below:

"Column 20, lines 16-17, for "carboxylic acid-containing" read --poly(acrylic acid)--.

Column 20, lines 18-19, for "carboxylic acid-containing" read --poly(acrylic acid)--."

Signed and Sealed this

Tenth Day of November, 1992

*Attest:*

DOUGLAS B. COMER

*Attesting Officer*     *Acting Commissioner of Patents and Trademarks*